US007955341B2

(12) United States Patent
Cerundolo (10) Patent No.: US 7,955,341 B2
(45) Date of Patent: *Jun. 7, 2011

(54) METHOD AND APPARATUS FOR PROVIDING SUTURE IN A PASSAGEWAY

(75) Inventor: Daniel Cerundolo, Hingham, MA (US)

(73) Assignee: Arthroscopic Innovations LLC, Weymouth, MA (US)

( * ) Notice: Subject to any disclaimer, the term of this patent is extended or adjusted under 35 U.S.C. 154(b) by 770 days.

This patent is subject to a terminal disclaimer.

(21) Appl. No.: 11/799,972

(22) Filed: May 3, 2007

(65) Prior Publication Data

US 2007/0208356 A1 Sep. 6, 2007

Related U.S. Application Data (62) Division of application No. 11/110,004, filed on Apr. 20, 2005, now Pat. No. 7,771,441.

(51) Int. Cl.
*A61B 17/04* (2006.01)
*A61F 5/00* (2006.01)
*A61F 2/00* (2006.01)

(52) U.S. Cl. ........... 606/148; 606/86 R; 606/87; 606/96; 606/98; 606/232; 606/233

(58) Field of Classification Search .............. 606/86 R, 606/87, 96, 98, 148, 232, 233; 623/13.13, 623/13.14

See application file for complete search history.

(56) References Cited

U.S. PATENT DOCUMENTS

| 3,976,079 A | 8/1976 | Samuels et al. |
| 4,103,683 A | 8/1978 | Neufeld |
| 4,535,768 A | 8/1985 | Hourahane et al. |
| 4,633,869 A | 1/1987 | Schmieding |
| 4,672,957 A | 6/1987 | Hourahane |
| 4,722,331 A | 2/1988 | Fox |
| 4,739,751 A | 4/1988 | Sapega et al. |
| 4,781,182 A | 11/1988 | Purnell et al. |
| 4,920,958 A | 5/1990 | Walt et al. |
| 4,945,904 A | 8/1990 | Bolton et al. |
| 5,042,983 A | 8/1991 | Rayhack |

(Continued)

OTHER PUBLICATIONS

Office Action mailed Jan. 19, 2010 for U.S. Appl. No. 11/110,584.

*Primary Examiner* — (Jackie) Tan-Uyen T Ho
*Assistant Examiner* — Melissa Ryckman
(74) *Attorney, Agent, or Firm* — Wolf, Greenfield & Sacks, P.C.

(57) ABSTRACT

A surgical apparatus may include a guide apparatus to be used in an arthroscopic procedure and to interact with a passageway through a body portion formed by intersecting first and second holes that may lead into the body portion from different positions, e.g., from two different locations on a bone. The guide apparatus may include first and second guide members having first and second passages, respectively, that communicate with the first and second holes. The surgical apparatus may also include a suture retriever arranged to retrieve, from the second passage, a suture fed into the first passage. A method may include forming a passageway including first and second intersecting holes. First and second guide tubes may be positioned relative to the first and second holes, a suture or suture-like material may be provided into the first guide tube, and the suture or suture-like material may be retrieved from the second guide tube.

15 Claims, 5 Drawing Sheets

U.S. PATENT DOCUMENTS

| | | | |
|---|---|---|---|
| 5,112,337 | A | 5/1992 | Paulos et al. |
| 5,163,940 | A | 11/1992 | Bourque |
| 5,178,621 | A | 1/1993 | Cook et al. |
| 5,211,647 | A | 5/1993 | Schmieding |
| 5,217,471 | A | 6/1993 | Burkhart |
| 5,222,962 | A | 6/1993 | Burkhart |
| 5,234,434 | A | 8/1993 | Goble et al. |
| 5,269,786 | A | 12/1993 | Morgan |
| 5,320,626 | A | 6/1994 | Schmieding |
| 5,330,468 | A * | 7/1994 | Burkhart ................. 606/96 |
| 5,334,205 | A | 8/1994 | Cain |
| 5,350,383 | A | 9/1994 | Schmieding et al. |
| 5,368,596 | A | 11/1994 | Burkhart |
| 5,403,321 | A | 4/1995 | DiMarco |
| 5,425,733 | A | 6/1995 | Schmieding |
| 5,431,651 | A | 7/1995 | Goble |
| 5,466,243 | A | 11/1995 | Schmieding et al. |
| 5,575,801 | A | 11/1996 | Habermeyer et al. |
| 5,601,562 | A | 2/1997 | Wolf et al. |
| 5,603,716 | A | 2/1997 | Morgan et al. |
| 5,620,449 | A | 4/1997 | Faccioli et al. |
| 5,626,613 | A | 5/1997 | Schmieding |
| 5,643,320 | A | 7/1997 | Lower et al. |
| 5,681,333 | A | 10/1997 | Burkhart et al. |
| 5,683,401 | A | 11/1997 | Schmieding et al. |
| 5,690,677 | A | 11/1997 | Schmieding et al. |
| 5,743,916 | A | 4/1998 | Greenberg et al. |
| 5,746,752 | A | 5/1998 | Burkhart |
| 5,766,179 | A | 6/1998 | Faccioli et al. |
| 5,833,691 | A | 11/1998 | Bimman |
| RE36,020 | E | 12/1998 | Moore et al. |
| 5,918,604 | A | 7/1999 | Whelan |
| 5,919,196 | A | 7/1999 | Bobic et al. |
| 5,951,559 | A | 9/1999 | Burkhart |
| 5,964,783 | A | 10/1999 | Grafton et al. |
| 5,993,451 | A | 11/1999 | Burkhart |
| 6,027,523 | A | 2/2000 | Schmieding |
| 6,039,742 | A | 3/2000 | Krettek et al. |
| 6,074,403 | A | 6/2000 | Nord |
| 6,113,604 | A | 9/2000 | Whittaker et al. |
| 6,117,162 | A | 9/2000 | Schmieding et al. |
| 6,120,511 | A | 9/2000 | Chan |
| 6,132,433 | A | 10/2000 | Whelan |
| 6,214,031 | B1 | 4/2001 | Schmieding et al. |
| 6,267,766 | B1 | 7/2001 | Burkhart |
| 6,270,503 | B1 | 8/2001 | Schmieding |
| 6,319,270 | B1 | 11/2001 | Grafton et al. |
| 6,371,124 | B1 | 4/2002 | Whelan |
| 6,387,129 | B2 | 5/2002 | Rieser et al. |
| 6,416,518 | B1 | 7/2002 | DeMayo |
| 6,461,373 | B2 | 10/2002 | Wyman et al. |
| 6,511,499 | B2 | 1/2003 | Schmieding et al. |
| 6,517,552 | B1 | 2/2003 | Nord et al. |
| 6,517,564 | B1 | 2/2003 | Grafton et al. |
| 6,524,317 | B1 | 2/2003 | Ritchart et al. |
| 6,537,319 | B2 | 3/2003 | Whelan |
| 6,540,750 | B2 | 4/2003 | Burkhart |
| 6,544,281 | B2 | 4/2003 | ElAttrache et al. |
| 6,575,976 | B2 | 6/2003 | Grafton |
| 6,592,588 | B1 | 7/2003 | Bobic et al. |
| 6,616,665 | B2 | 9/2003 | Grafton et al. |
| 6,616,674 | B2 | 9/2003 | Schmieding |
| 6,623,524 | B2 | 9/2003 | Schmieding |
| 6,629,977 | B1 | 10/2003 | Wolf |
| 6,641,597 | B2 | 11/2003 | Burkhart et al. |
| 7,569,059 | B2 * | 8/2009 | Cerundolo ................. 606/86 R |
| 2003/0065391 | A1 * | 4/2003 | Re et al. ................. 623/13.14 |

* cited by examiner

METHOD AND APPARATUS FOR PROVIDING SUTURE IN A PASSAGEWAY

This application is a divisional application of U.S. application Ser. No. 11/110,004, filed Apr. 20, 2005, which is hereby incorporated by reference in its entirety.

BACKGROUND OF INVENTION

1. Field of Invention

This invention relates to methods and apparatus for providing suture in a passageway.

2. Discussion of Related Art

Figure 1:
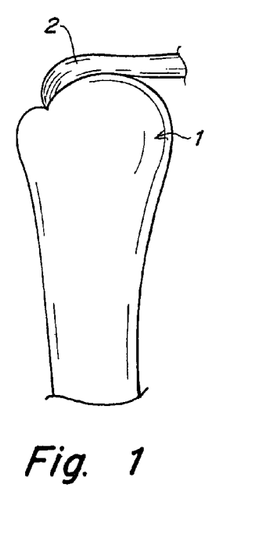
FIG. 1 is a schematic diagram of a head of a humerus and attached rotator cuff tendon.
Figure 2:
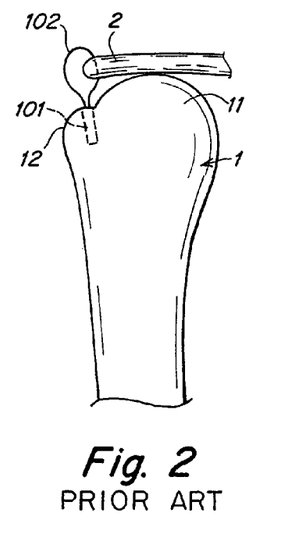
FIG. 2 shows a prior art technique for repairing a rotator cuff injury.

Providing a passageway in a body portion, such as a bone, is a common procedure in surgical repair. For example, tendon damage frequently requires surgery for repair, e.g., to reattach a torn or separated tendon to the bone to which the tendon would normally be attached. In some cases, reattachment of the tendon or other material is performed using a passageway through bone, i.e., a transosseous tunnel. For example, rotator cuff injuries typically involve damage to the rotator cuff tendon such that the tendon, or at least a portion thereof, requires reattachment to the humerus. FIG. 1 shows a schematic diagram of a humerus 1 and a portion of a rotator cuff tendon 2 that is normally attached to the head of the humerus. In one type of damage to the rotator cuff, the tendon 2 may detach or be partially torn from the humerus 1, such as that shown schematically in FIG. 2. Such damage may be repaired by reattaching the rotator cuff tendon to the humerus 1 by a suture or other fixation so that the body's normal healing processes can naturally effect reattachment of the tendon to the bone. One repair technique for reattaching the rotator cuff 2 to the humerus 1 involves forming a hole in the bone and fixing an anchor 101 at a margin between the articulating portion 11 of the humerus 1 and the humerus' greater tuberosity 12. A suture 102 is secured to the rotator cuff 2 and the anchor 101, and the suture 102 is tensioned so that the rotator cuff 2 is held in place close to the humerus 1. Thereafter, the body may reestablish the proper attachment of the rotator cuff 2 to the humerus 1.

In another repair technique, a passageway may be formed through the humeral head, e.g., extending from a point at the margin to a location on the lateral side of the humerus. U.S. Pat. No. 5,330,468 discloses a drill guide for forming such a passageway in the humeral head and subsequently feeding suture through the passageway. One end of a suture placed in the rotator cuff may be passed through the passageway, and another end of the suture may be extended around the greater tuberosity (or passed through another adjacent passageway in the bone), and the two ends joined together to secure the tendon in place.

SUMMARY OF INVENTION

Aspects of the invention provide a guide apparatus for use with a passageway in a body portion, such as a portion of bone, where the passageway is formed by two intersecting holes. The guide apparatus may be arranged so that two guide members can be associated with the passageway in such a way (e.g., partially positioned in the passageway) that passages in the guide members are positioned adjacent each other in the passageway, e.g., to facilitate passing a suture from one guide member to the other. The guide apparatus may alternately, or additionally, be used to form all or part of the passageway in the body portion. For example, guide members in the apparatus may be used to perforate the body portion, guide the movement of a perforator, and/or define the starting point of an opening when forming one or two holes that form the passageway. The guide apparatus may be used in an arthroscopic or open surgical procedure.

In one aspect of the invention, a surgical apparatus may include a guide apparatus constructed and arranged to be used in an arthroscopic procedure and to interact with a passageway through a body portion formed by intersecting first and second holes. The first and second holes may lead into the body portion from different positions, e.g., from two different locations on a bone. The guide apparatus may include first and second guide members having first and second passages, respectively, that communicate with the first and second holes, respectively. The surgical apparatus may also include a suture retriever arranged to retrieve, from the second passage, a suture fed into the first passage.

In another aspect of the invention, a method for surgical repair includes forming a passageway through a body portion, where the passageway is formed by first and second intersecting holes in the body portion. First and second guide tubes may be respectively positioned relative to the first and second holes. A suture or suture-like material may be provided into the first guide tube, and the suture or suture-like material may be retrieved from the second guide tube.

In one aspect of the invention, an apparatus for providing a passageway in a surgical procedure includes a reference structure, and first and second guide members each having distal and proximal ends and a passage leading to the distal end. The first guide member may be adapted to be arranged in a first position relative to the reference structure, and the second guide member may be adapted to be arranged in a second position relative to the reference structure. When in the first and second positions, the first and second guide members may be arranged so that the first and second passages are adjacent, e.g., the distal ends of the first and second guide members may be adjacent each other. This arrangement may allow for the first and second guide members to be used in forming a passageway in a body part, such as a portion of bone, and/or may provide a passageway for passing a suture or suture-like material from the first guide member to the second guide member. For example, one of the guide members may be used to guide the movement of a perforator, such as a drill, punch or awl, so as to form the passageway in a desired location. Alternately, or in addition, the guide apparatus may be used with a pre-formed passageway to pass a suture or suture-like material through the passageway.

In one aspect of the invention, a method for performing a surgical repair includes providing a first hole in a body portion, positioning a guide relative to the first hole, and forming a second hole using the guide to define a location of the second hole so that the second hole intersects with the first hole and forms a passageway through the body portion. The guide may be used to provide a suture or suture-like material through the passageway, and a repair suture may be secured to a material to be secured relative to the body portion. At least a portion of the repair suture may be positioned in the passageway, and the material secured relative to the body portion using the repair suture.

In another aspect of the invention, a method for forming a passageway in bone includes providing a first hole into bone of a humerus, and securing a first guide member relative to the first hole. The first guide member may be positioned with respect to a reference structure, and a second hole may be formed in the bone using the reference structure to define the location of the second hole relative to the first hole. The second hole may be formed so as to intersect the first hole and form a passageway through the bone. At least a portion of a suture may be passed through the passageway, and a rotator cuff tendon may be secured relative to the bone using the suture.

BRIEF DESCRIPTION OF DRAWINGS

Various aspects of the invention are described with reference to illustrative embodiments, wherein like numerals reference like elements, and wherein.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. Also, the term "guide" or "guiding" as used herein means actually guiding an element in its movement, and/or providing some reference for the location of an element. For example, "guiding" the formation of a hole in a body portion may mean guiding a bone perforator when actually forming the hole and/or providing a starting location for the hole formation.

Various aspects of the invention are described below with reference to specific embodiments. For example, aspects of the invention are described in the context of performing a rotator cuff repair. However, it should be understood that aspects of the invention are not necessarily restricted to rotator cuff repair techniques, or even to surgical techniques performed on a shoulder. Rather, various aspects of the invention may be used in any suitable surgical procedure. In addition, various aspects of the invention may be used alone, and/or in combination with any other aspects of the invention.

In another aspect of the invention, a passageway formed through a body portion, such as bone, may be made by first and second intersecting holes. That is, the first and second holes may be formed into the body portion so each originate at different starting points and intersect within the body portion. The holes may be formed at an angle to each other or may be colinear. A guide may be used to define the location of the first and/or second hole, e.g., may be used to guide the movement of a bone perforator when forming the first and/or second holes, and/or may be used to locate a starting point for the formation of the first or second holes. In addition, or alternately, the guide may be used to pass a suture through the passageway. For example, a portion of the guide may be secured relative to one or both of the holes and a suture or other material may be passed through the guide portion when passing the suture or other material through the passageway.

In one aspect of the invention, a guide apparatus may be used to form one or two holes used to form a passageway in a body portion and/or to pass a suture or other material through the passageway. For example, a first guide member may be secured relative to a first hole formed in bone. A second guide member may be arranged so that its orientation relative to the first guide member is known. The second guide member may be used to guide the identification of a starting point for the formation of the second hole and/or guide the movement of a perforator or other device to form a second hole so that the orientation of the second hole is arranged in a known way relative to the first hole.

Alternately, the second guide member may be secured relative to a second hole that intersects with the first hole. The first and second guide members may be positioned relative to each other, e.g., using a reference structure, so that distal ends of the guide members are positioned adjacent each other in the passageway. Suture or other material may be introduced into one of the guide members and fed to a point adjacent the other guide member. The suture or other material may be retrieved from the guide member, for example, by a hook-shaped member, grasper or other suture retriever.

Various aspects of the invention may be used in an open surgical procedure or in a closed procedure, such as an arthroscopic procedure. For example, a guide apparatus may be used in an open or closed procedure as an aid in forming a passageway through a body portion, for passing a suture or other material through a passageway, or for both forming a passageway and passing a suture or other material through the passageway. In a closed procedure, each guide member in the apparatus may be passed through respective portals. Portions of the guide apparatus may remain outside of the body, however, such as the reference structure. Also, various aspects of the invention may be used in any suitable surgical or other procedure involving any suitable body portions, such as bone, muscle, skin, vascular structures, digestive structures, or other tissue, implants, mesh, or other medical devices, etc.

These and other aspects of the invention will be apparent from the following description.

Figure 3:
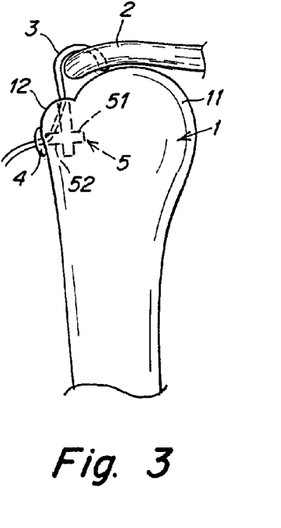
FIG. 3 is a schematic diagram of a tissue repair arrangement in accordance with an aspect of the invention.

FIG. 3 shows a schematic diagram of a surgical repair in accordance with aspects of the invention. As discussed above, although aspects of the invention are described with reference to a rotator cuff repair for ease of reference and understanding, aspects of the invention may be used in any surgical or other procedure, and may involve any suitable body portions, such as bone, muscle, other tissue or combinations thereof, vascular structures, digestive structures, medical implants or other devices, etc. Thus, aspects of the invention are in no way limited to the specific embodiments and examples described herein.

In this illustrative embodiment, a rotator cuff tendon 2 is secured by a suture 3 relative to a humerus 1. The suture 3 is placed in the tendon 2, for example, using a mattress stitch or other arrangement, and is passed through a passageway 5 formed through the humerus 1. In this embodiment, the passageway 5 is formed by first and second intersecting holes. A first hole 51 is formed vertically as shown in FIG. 3 from a first opening at or near a margin between the articulating surface 11 and the greater tuberosity 12 of the humerus 1. The second hole 52 is formed horizontally as shown in FIG. 3 from a lateral position on the humerus 1. The suture 3 is secured at the second opening of the second hole using a suture fixation device 4 that is positioned adjacent the second opening. Although in this embodiment the first and second holes 51 and 52 are arranged at approximately right angles, the first and second holes may be arranged at any suitable angle and may be colinear (i.e., at a 180 degree angle relative to each other).

A wire, other material or the suture 3 may be manipulated in the passageway 5 so as to cut through or crush the relatively soft cancellous bone of the humerus in the passageway 5 so that the suture follows a relatively straight path between the first and second openings into the first and second holes 51 and 52. The relatively straight pathway may be formed by a "flossing" operation, such as by using a wire that is passed through the passageway 5 and is manipulated, e.g., tensioned and reciprocally drawn between the first and second openings, so as to cut through or crush the cancellous bone, thereby forming a relatively straight path for the suture 3.

When deciding where to locate the first hole 51 for the passageway 5, a surgeon often will wish to first determine the final position for the tissue relative to the bone. To do so, the surgeon may wish to place a suture in the tendon 2 and tension the suture 3 (and thus the tendon 2) so that a desired position for the first hole 51 may be determined, e.g., based on the position of the tendon 2 relative to the bone when under tension.

Figure 4:
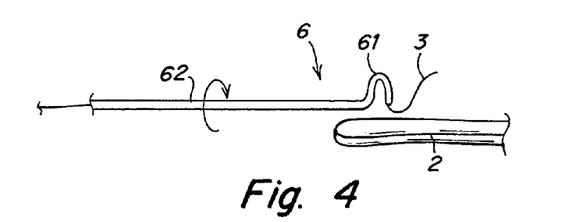
FIGS. 4-6 show the use of a needle for placing a suture in a tissue in accordance with the invention.
Figure 5:
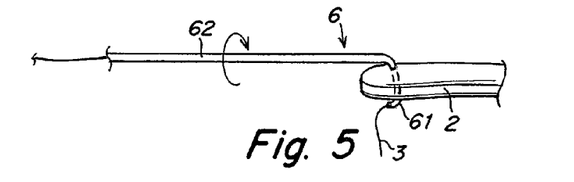
Figure 6:
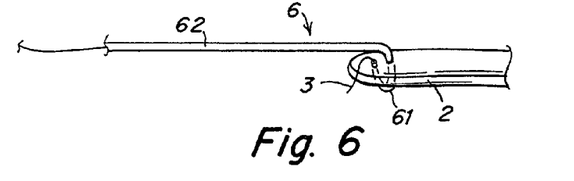

In various aspects of the invention, a suture may be placed in the tendon or other tissue 2 using any suitable technique, such as a standard suturing needle and forceps, specialized suturing devices, and so on. However, in one aspect of the invention, use of a needle having a hook-shaped or curved end portion may be preferred. FIGS. 4-6 show an embodiment of a needle 6 having a hook-shaped tissue penetrating portion 61 at a distal end in accordance with the invention. In the illustrated embodiment, the tissue penetrating portion 61 of the needle 6 has a semi-circular shape and is arranged at an angle, such as 90 degrees to a longitudinal axis of a straight portion 62 of the needle 6. The needle 6 may be formed as a hollow tube so that the suture 3 may pass through the needle 6. Suture may be loaded in the hollow portion of the needle 6 before the surgical procedure is begun, e.g., at the time of manufacture of the needle, or at any suitable time, such as during the surgical procedure. In some cases, the suture may be fed into the hollow portion of the needle 6 before the tissue penetrating portion 61 is formed, e.g., by bending a tube to form a curved end shape.

The arrangement of the needle 6 may allow placement of a mattress stitch in the tissue 2 by rotating the needle as shown in FIGS. 4-6 so that a tip of the tissue penetrating portion 61 passes through a top side of the tissue 2 and exits from a bottom side of the tissue 2 as shown in FIG. 5, and then passes upwardly through the tissue 2 to reemerge at a top side of the tissue 2 as shown in FIG. 6. At this point, the suture 3 extending from the tip of the tissue penetrating portion 61 may be grasped, such as by forceps or other gripping device, and the needle 6 may be rotated in reverse so as to again position the needle 6 as shown in FIG. 4, thereby leaving the suture 3 positioned in the tissue 2 to form a mattress stitch. During the passage of the suture, the tissue or other material may be held in place, or may be manipulated, by a grasper or other device inserted into the lumen of the cannula. The tissue or other material may also be held in place, or manipulated, by another device, such as a grasper or clamp positioned external to the cannula.

The tissue penetrating portion 61 of the needle 6 may have any suitable shape and may be arranged in a plane that is transverse at any angle to an axis of rotation of the tissue penetrating portion 61 when placing a suture in tissue. That is, although in the illustrated embodiment the tissue penetrating portion 61 has a semi-circular form that lies in a plane at 90 degrees to the rotation axis of the tissue penetrating portion 61 when placing a suture, the tissue penetrating portion 61 need not have a semi-circular form and may lie at any desired angle to the rotation axis. For example, the tissue penetrating portion 61 may be arranged so as to place an inclined mattress stitch in a tissue 2. Further, the needle 6 need not be used only to form a mattress stitch, but rather may be used to form any other suitable stitch type. Also, it is not necessary that the tissue penetrating portion 61 of the needle 6 lie in a single plane. Instead, the tissue penetrating portion 61 may not lie in a single plane, e.g., may have a corkscrew-type or partially helical configuration.

In one aspect of the invention, all or portions of a tissue repair procedure may be performed arthroscopically. In this case, and as is known in the art, one or more cannulas may be provided in one or more portals formed in the patient so as to provide access to the operative site. In one aspect of the invention, a needle used to place a suture in a tissue, such as the needle 6 shown in FIG. 4, may be used in an arthroscopic procedure. For example, the needle 6 may be secured to a cannula so that the needle may be operated by manipulation of the cannula.

Figure 7:
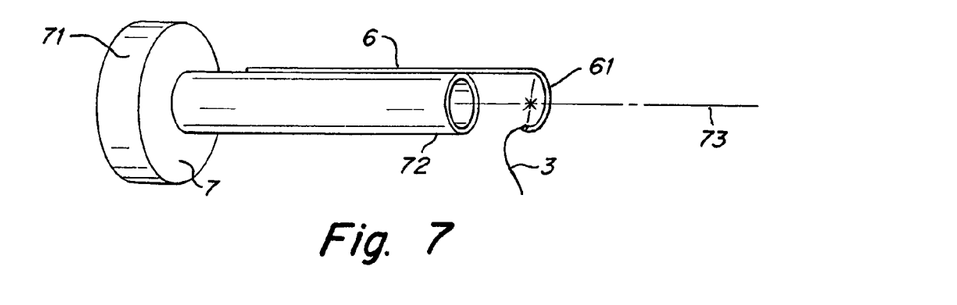
FIG. 7 shows a needle in engagement with a cannula in accordance with an aspect of the invention.

FIG. 7 shows an illustrative embodiment of a needle 6 that is secured to a cannula 7. The cannula 7 may have any suitable features found in cannulas used for closed or minimally-invasive surgical techniques, such as one or more valves to resist fluid flow through the cannula 7, an opening through which to introduce a fluid pressure or vacuum, spiral threads or other features on the cannula to aid in placement of the cannula in a portal and/or to help prevent inadvertent removal of the cannula from the portal, and so on. The cannula 7 may be arranged for any type of procedure, such as arthroscopic procedures.

The needle 6 may be secured to the cannula 7 in any suitable way. For example, the needle 6 may be molded into the body of the cannula 7, may be inserted into a wall of the cannula, may be secured by adhesive, welding, clamps, fasteners, interlocking channels, open channels, or any other suitable device. A proximal end of the needle 6 may terminate at any suitable point, such as midway between a proximal end 71 and a distal end 72 of the cannula 7 as shown, or, more preferably at a position proximal to the proximal end 71. By having the proximal end of the needle 6 positioned proximally of the cannula 7, a user may be better able to access the suture 3 entering the proximal end of the needle 6. The needle 6 may also be axially movable relative to the cannula, e.g., so that the tissue penetrating portion 61 may be moved axially so as to extend away from or toward the distal end 72 of the cannula 7. In addition, although the needle 6 is shown as positioned on an outer surface of the cannula 7, the needle 6, or at least a portion thereof, may be molded into the cannula 7, positioned within the cannula lumen, positioned within the cannula wall, may be arranged within a groove on the outer surface of the cannula, and so on. Although the needle 6 is shown as arranged in an approximately straight fashion along the length of the cannula 7, the needle 6 may be bent, curved or arranged in any suitable way, such as following a spiral path around an outer surface of the cannula 7.

In one illustrative embodiment, a semicircular-shaped tissue penetrating portion 61 of the needle 6 may be arranged relative to the cannula 7 so that a centerpoint of the semicircle lies on a central longitudinal axis 73 of the cannula lumen. Thus, when the cannula 7 is rotated about the central longitudinal axis 73, the tissue penetrating portion 61 may travel in a circular path about the axis 73. However, it should be understood that the tissue penetrating portion 61 may be arranged in any suitable way relative to the axis 73. Further, a plane in which the tissue penetrating portion 61 lies (if present) may be arranged at any angle transverse to the axis 73, and thus need not be arranged at an angle of 90 degrees to the axis 73, as shown in FIG. 7.

In one aspect of the invention, the needle 6 may be removeably engaged with the cannula 7 so that the needle 6 can be selectively engaged or disengaged with the cannula 7. For example, a cannula 7 may be positioned in a portal in use during a surgical procedure without an attached needle 6. At some point during the procedure, the surgeon may wish to attach a needle 6 to the cannula 7 and manipulate the cannula 7 so as to use the needle 6 to place a suture in a tissue. The needle 6 may be secured to the cannula while the cannula remains in place in the portal (e.g., by inserting the needle 6 into the cannula lumen), or the cannula may be removed from the portal, the needle attached, and the cannula and attached needle inserted into the portal.

Figure 8:
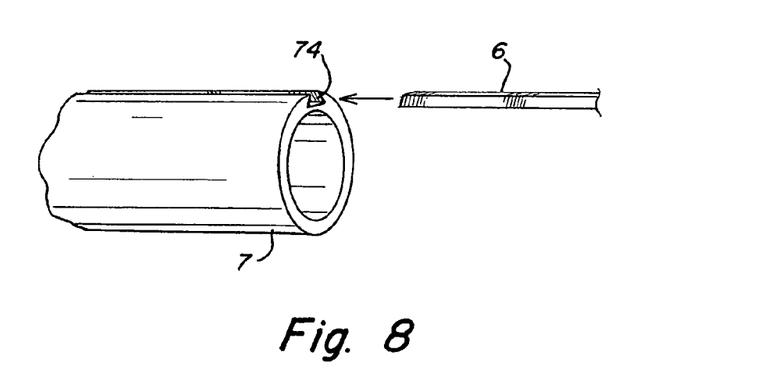
FIG. 8 shows an illustrative arrangement for engaging a needle with a cannula in one embodiment.

FIG. 8 shows one illustrative embodiment in which a needle 6 may be removably secured to a cannula 7. In this embodiment, the cannula 7 includes a dovetail-shaped groove 74 into which a correspondingly shaped portion of the needle 6 is inserted. The complementary locking arrangement used by the cannula 7 and the needle 6 need not necessarily be dovetail-shaped as shown in FIG. 8, but rather may have any suitable arrangement. For example, the cannula 7 may have an oval-shaped channel formed in the cannula wall that engages with a complementary oval-shaped portion of the needle 7. Thus, the needle 6 may be selectively secured to the cannula 7 so that rotation or other manipulation of the cannula 7 can cause the needle to be manipulated so as to place a suture in a tissue. The complementary locking arrangement between the needle 6 and the cannula 7 may also allow for axial movement of the needle 6 relative to the cannula 7, e.g., so the tissue penetrating portion 61 can be moved relative to the distal end 72 of the cannula 7.

Figure 9:
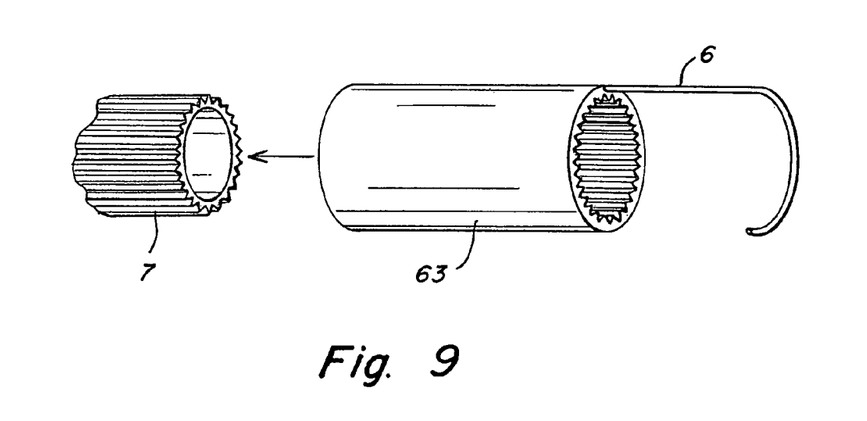
FIG. 9 shows an illustrative arrangement for engaging a sleeve and needle assembly with a cannula in accordance with another embodiment.

FIG. 9 shows an alternative embodiment in which a needle 6 is fixed to a sleeve member 63 that has one or more complementary locking features that mesh with or otherwise engage with complementary features on the cannula 7. In this embodiment, the complementary locking features have a tooth-like or gear-like form, but the complementary locking features may be arranged in any suitable way. Accordingly, in this embodiment, the needle 6 may be secured to the cannula 7 by sliding the sleeve 63 over the distal end 72 of the cannula 7. It will be understood that rather than having a sleeve 63 that fits over the cannula 7, the sleeve 63 may fit within the internal lumen of the cannula 7, or within a slot in the cannula 7, if desired.

Once a suture is placed in the tissue, such as a rotator cuff tendon, the tissue may be tensioned to determine a location for the opening of the first hole 51 to be formed in the bone. When performing a rotator cuff repair, typically, a first hole 51 of the passageway 5 will be formed vertically from a superolateral position so that the first hole 51 is generally aligned along the length of the humerus 1 and extends into the bone from an opening formed at the margin between the articulating surface 11 and the greater tuberosity 12. This first hole 51 may be formed using a perforator, such as a drill, awl, punch or other suitable device. As with other procedures performed, the first hole 51 may be formed using an arthroscopic portal at a superolateral position, or may be formed in an open surgical procedure.

Figure 10:
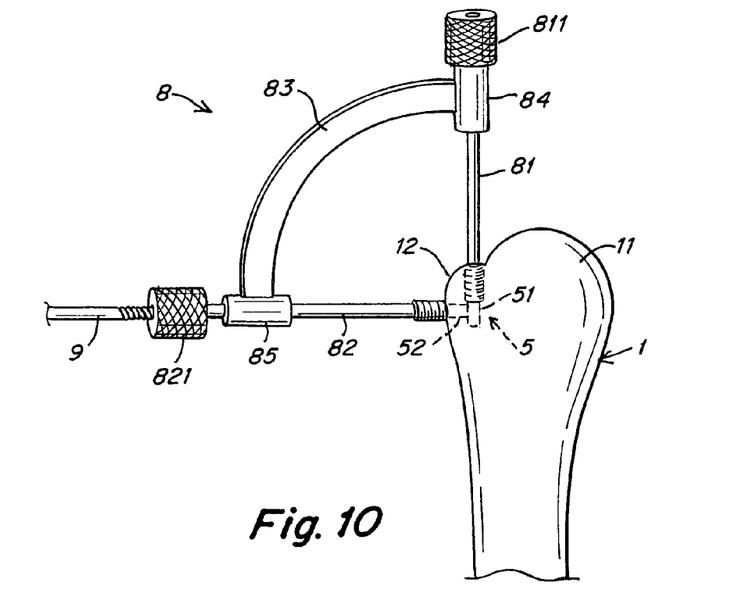
FIG. 10 shows a guide apparatus used in forming a passageway in accordance with the invention.

In accordance with an aspect of the invention, a guide apparatus may be used to form the first and/or second holes of the passageway (e.g., used to locate a starting point or opening for the first and second holes, used to orient a bone perforator when making the holes, or used alone to form the first and/or second holes), or may be used to help feed a suture or suture-like material through the passageway. For example, a first guide member 81 may be secured relative to the first hole 51, as shown in FIG. 10. The first guide member 81 may be part of a guide apparatus 8 used to guide the formation of holes used to form a passageway in bone and/or to pass a suture or other material through the passageway. In the illustrated embodiment, the first hole 51 has been formed in a vertical direction along the length of the humerus 1, e.g., by drilling the hole in a freehand manner. (Alternately, the first hole 51 may be formed by forcing the first guide member 81 into the bone as with an awl or similar instrument.) The first guide member 81 may include a feature to help secure the first guide member 81 relative to the first hole 51, such as a threaded distal end that allows the first guide member 81 to be screwed into the bone to a desired depth in the first hole 51. It should be understood, however, that the distal end of the first guide member 81 need not be threaded, but instead may unthreaded and inserted into the first hole 51. Alternately, the distal end of the first guide member 81 may be positioned outside of, but adjacent to, the first hole 51 so that a lumen in the first guide member 81 aligns with the first hole 51. The first hole 51 may be formed so as to be deeper than thought to be needed, e.g., 0.5 cm deeper than a hole depth believed to be required. This overdrilling of the first hole 51 may allow for more flexibility in positioning the first guide member 81 to a desired depth in the bone.

The first guide member 81 may be arranged with respect to a reference structure 83 used to position first and second guide members 81 and 82 relative to each other with respect to the passageway 5, as is discussed in more detail below. In this illustrative embodiment, the reference structure 83 is arranged so that the first and second guide members 81 and 82 are positioned at a 90 degree angle relative to each other when engaged with the reference structure 83. However, the reference structure 83 may be arranged in any suitable way so as to orient the first and second guide members 81 and 82 at any desired angle relative to each other, including arranging the first and second guide members 81 and 82 in a co-linear fashion. Further, the reference structure 83 may be made so as to be adjustable, thereby allowing the orientation of the first and second guide members 81 and 82 to be changed. For example, the arc-shaped connecting portion of the reference structure 83 may be made so as to be adjustable in length, e.g., having one arc-shaped portion sliding relative to another arc-shaped portion to allow adjustment of the length of the connecting portion. Alternately, or in addition, engagement portions 84 and 85 of the reference structure 83 that engage with the first and second guide members 81 and 82 may be adjustable in orientation relative to the arc-shaped connecting portion. In short, the reference structure 83 may be arranged in any suitable way so as to allow adjustment in the orientation of the guide members 81 and 82.

In this illustrative embodiment, the engagement portions 84 and 85 include sleeves that receive at least a portion of the guide members 81 and 82, e.g., the guide members 81 and 82 may be received in bores in the sleeves. The sleeves may be arranged so that the guide members 81 and 82 are movable linearly along their longitudinal axes and rotationally about their longitudinal axes relative to the engagement portions 84 and 85, but otherwise may be relatively restricted in their range of movement. When a stop on the first guide member 81, such as a knob 811 on the proximal end of the guide member 81, contacts an engagement surface on the reference structure, such as a portion of the engagement portion 84, the second guide member 82 may be positioned by the reference structure 83 so that its longitudinal axis passes a point adjacent the extreme distal end of the first guide member 81. Thus, the second guide member 82 may be used to guide the use of a perforator 9 (such as a drill, punch, awl or other bone perforating device) so that the perforator 9 forms a second hole 52 that intersects with the first hole 51 at a location adjacent the distal end of the first guide member 81. As discussed above, the guide member 82 may guide the movement of the perforator 9, e.g., guide the movement of a drill or punch inserted into a lumen of the guide member 82 as shown, or may guide a starting location for forming the second hole, e.g., be used to mark or otherwise determine a starting location for the perforator 9, but otherwise not interact with the perforator 9. By adjusting the depth of the first guide member 81 in the first hole 51, the location where the second hole 52 is formed can be adjusted in position (e.g., in a vertical direction as shown in the figures). For example, by screwing the first guide member 81 into or out of the first hole 51, a surgeon may select a location where the second hole 52 is to be formed in the bone.

In another embodiment, the engagement portion 85 may itself function as a perforator guide with the second guide member 82 being withdrawn from the engagement portion 85. Although in this illustrative embodiment the engagement portions 84 and 85 are shown as relatively short cylindrical sleeves, the engagement portions 84 and 85 may be arranged in any suitable way, e.g., may be elongated so as to more closely approach the humerus 1 and provide improved guidance for a perforator 9 and/or the first and second guide members 81 and 82. Further, the first guide member 81 may be arranged so that is rotationally movable about its longitudinal axis relative to the reference structure 83, but is otherwise held by the engagement portion 84 so that the first guide member 81 is not movable axially. This may aid is appropriately positioning the first guide member 81 and reference structure 83 when forming the second hole 52.

Upon formation of the second hole 52, the second guide member 82 may be screwed into the second hole 52 until a stop on the second guide member 82, such as a knob 821 at a proximal end of the guide member 82, contacts an engagement surface on the engagement portion 85, such as a portion of the sleeve. In this configuration shown in FIG. 11 (stops on the first and second guide members 81 and 82 engaged with respective engagement surfaces on the reference structure 83), the extreme distal ends of the first and second guide members 81 and 82 may be adjacent to each other in the passageway 5 formed by the first and second holes 51 and 52. Accordingly, a surgeon may be assured that if the first and second guide members 81 and 82 are positioned within the bone and stops on the guide members 81 and 82 are respectively in contact with appropriate engagement surfaces on the guide apparatus 8, the extreme distal ends of the guide members 81 and 82 will be positioned adjacent each other. Thus, the surgeon may be assured that a wire 10 or other element may be fed into one of the guide members and retrieved from the other of the guide members, e.g., using a retriever 21 having a hook at a distal end. Such an arrangement may be advantageous when using the guide apparatus 8 in an arthroscopic procedure where the operative site may not be easily visualized.

Figure 11:
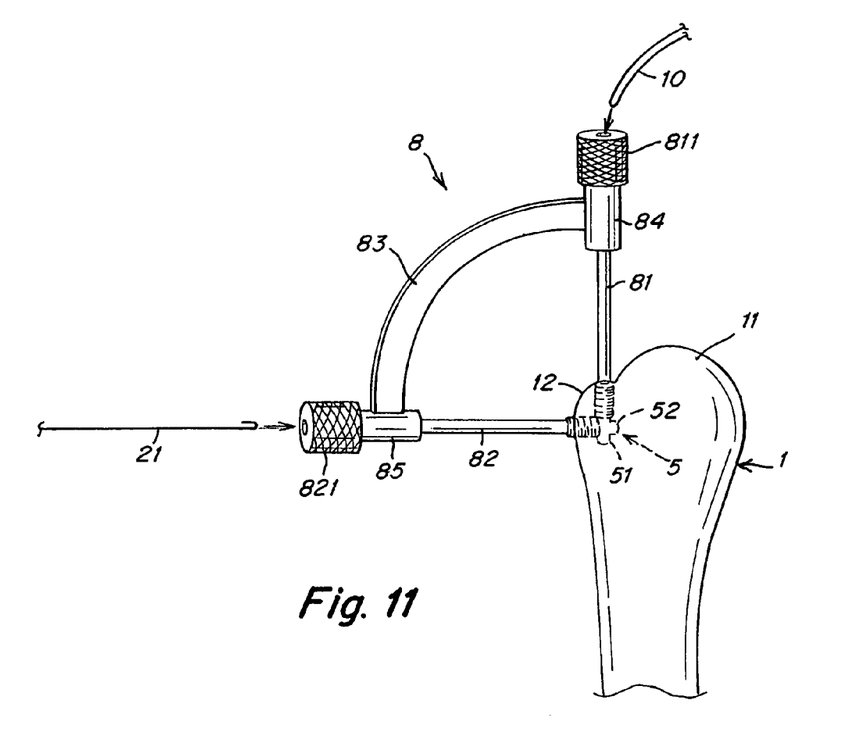
FIG. 11 shows the use of a guide apparatus for passing a suture or other element through a transosseous passageway in accordance with the invention.

Although in the above embodiment, stops on the first and second guide members 81 and 82 contact corresponding engagement surfaces on the engagement portions 84 and 85, the guide members 81 and 82 may be positioned relative to the reference structure 83 in any suitable way. For example, the guide members 81 and 82 may have indicator marks on them that may be aligned with a portion of the engagement portions 84 and 85, respectively. The alignment of certain indicator marks on the guide members 81 and 82 may be used to indicate, for example, that the distal ends of the guide members 81 and 82 are adjacent each other. Those of skill in the art will understand that the position of the guide members 81 and 82 relative to the reference structure 83 and relative to each other may be determined in other ways. For example, the first and second guide members 81 and 82 need not necessarily be positioned so that their distal ends are adjacent in the passageway to assist in feeding a suture from one guide member to the other. Instead, the first and second guide members 81 and 82 may be made to suitably communicate with the passageway in any way so as to facilitate feeding of the suture.

In this illustrative embodiment, the first guide member 81 is shown as having a smaller diameter (at least at the distal end) than the second guide member 82. This may allow the guide apparatus 8 to be used with an arrangement where the first hole 51 is smaller than the second hole 52. A relatively small first hole 51 may allow for more rapid healing and/or provide additional space for other holes in the margin, if needed. However, it should be understood that the guide apparatus 8 and/or the holes that form the passageway 5 may be made in any suitable way, e.g., the first and second holes 51 and 52 may have the same diameter or the first hole 51 may have a larger diameter than the second hole 52.

The guide apparatus 8 may also include additional guide members if desired, e.g., to provide for the formation of a third hole that is formed in the margin and is approximately parallel to the first hole 51, but also intersects with the second hole 52. Similarly, the guide apparatus 8 may include two pairs of guide members like that in the illustrative embodiment that are arranged to form side-by-side passageways 5 in the bone or other body portion.

Although in this illustrative embodiment, the guide apparatus 8 is used to guide the formation of the second hole 52, the guide apparatus 8 need not necessarily be used to guide the formation of the second hole 52. That is, the guide apparatus 8 may be used only to help feed the wire 10, suture or other material through a passageway that is pre-formed in the bone or other body portion. In addition, the first and second guide members 81 and 82 may be arranged so that the members 81 and 82 can be secured in a body portion without requiring holes to be predrilled or otherwise formed. Thus, in one embodiment, the first and second guide members 81 and 82 may be arranged like an awl or other device capable of forming a hole in a body portion, e.g., capable of being forced into bone, forming the passageway 5 by their entry and/or providing a means to help feed a wire, suture or other material through the passageway 5.

Figure 12:
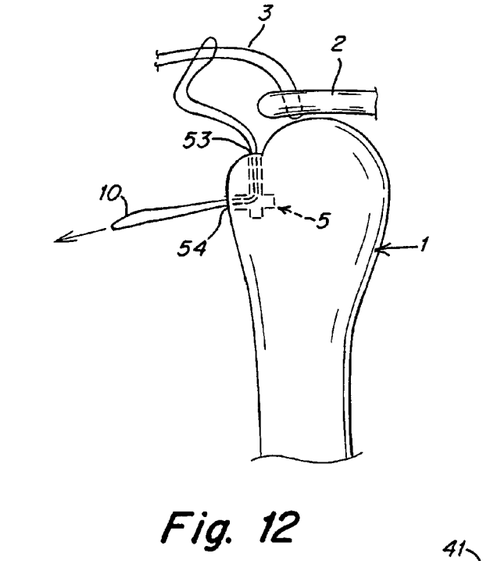
FIG. 12 shows a technique for passing a suture placed in a tissue through a passageway.

Once the wire 10, suture or other material has been passed through the passageway 5, as shown in FIG. 12, the wire 10 may be used to pull the suture 3 through the passageway 5. Prior to being used to pull the suture 3 through the passageway 5, the wire 10 or other material may be used to create a relatively straight pathway for the suture 3 once the suture 3 is tensioned and fixed in place. For example, the wire 10 may be tensioned between the first and second openings 53 and 54 of the first and second holes 51 and 52 or otherwise manipulated so as to cut or crush the body portion, e.g., bone, between the first and second openings 53 and 54. Such manipulation of the wire 10 may perform a kind of "flossing" effect in the bone, allowing the suture 3 to follow a more straight pathway through the passageway 5, reducing the length of suture 3 needed between the rotator cuff 2 and a point of fixation of the suture 3, e.g., near the second opening 54. The wire 10 may have barbs or other saw-like features to aid in cutting bone and forming the pathway. Of course, the more straight pathway could be formed by manipulating the suture 3 itself, e.g., by tensioning the suture 3 when securing the tendon or other material. Reducing the length of suture 3 in the passageway 5 may improve the suture's ability to maintain appropriate tension on the rotator cuff 2, e.g., by reducing the amount of stretch of the suture when under tension.

Figure 13:
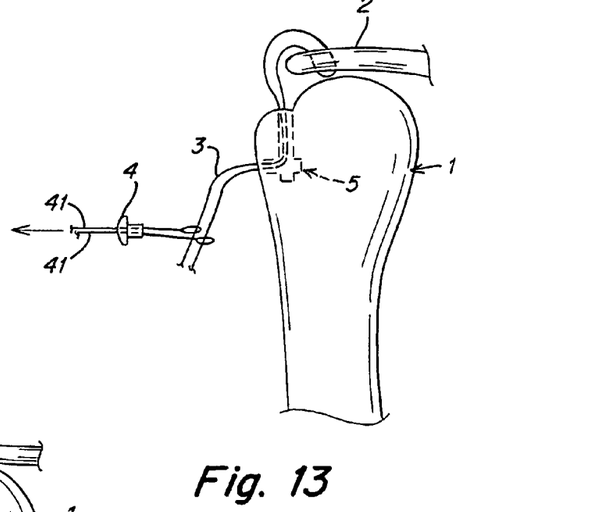
FIG. 13 shows the engagement of a suture with a suture fixation device in accordance with the invention.

After the suture 3 has been passed through the passageway 5, the suture 3 may be engaged with a suture fixation device 4 as shown in FIG. 13. Although use of a suture fixation device is not required, the suture fixation device 4 may improve an ability to securely fixate the suture 3 (and the tissue 2) relative to the bone. The suture fixation device 4 may be arranged in any suitable way, but in this illustrative embodiment has an arrangement similar to a button. For example, the suture fixation device 4 may have two through holes formed in a disk-shaped member through which leading ends of the suture 3 are passed. The suture ends 3 may be passed through respective holes in the suture fixation device 4 using one or more feed members 41. The feed members 41 may have an elongated shape that is passed through a respective hole in the suture fixation device 4. A loop at one end of the feed member 41 may receive an end of the suture 3 and thereafter the feed member 41 may be pulled through a respective hole in the suture fixation device 4 so as to pull the suture 3 through the hole. Of course, it should be understood that the suture 3 may be fed through the suture fixation device 4 in any other suitable way. When performing this technique arthroscopically, the suture 3 may be fed through the suture fixation device 4 either inside or outside of the body cavity.

Figure 14:
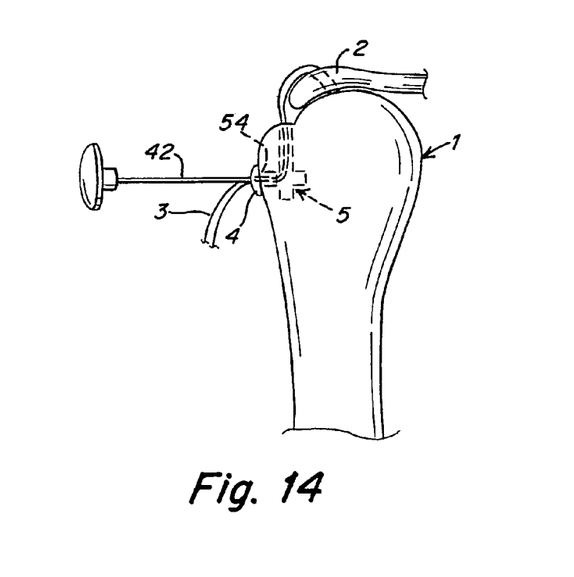
FIG. 14 shows the placement of a suture fixation device relative to the bone in accordance with the invention.
Figure 15:
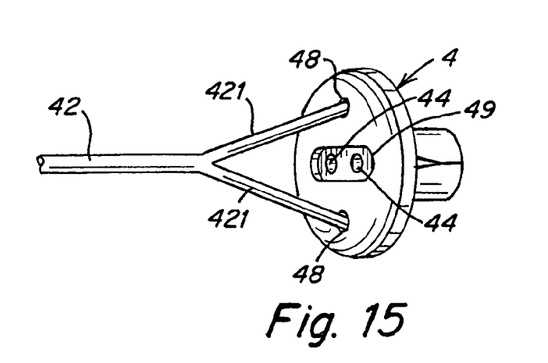
FIG. 15 shows a suture fixation device engagement tool in engagement with a suture fixation device in accordance with the invention.

As shown in FIG. 14, after the suture 3 is engaged with the suture fixation device 4, the suture fixation device 4 may be positioned relative to the second opening 54 of the passageway 5 using an applier 42 which removably engages with the suture fixation device 4 and may be selectively disengaged from the suture fixation device when the suture fixation device 4 is positioned as desired. As shown in FIG. 15, the applier 42 may have a pair of tines 421 that engage with recesses or other features on the suture fixation device 4 so as to removably engage with the suture fixation device 4. The tines 421 may be resilient so that the tines are squeezed together when engaged with the suture fixation device 4. Thus, an elastic force biasing the tine ends apart may help maintain engagement of the tines with the grooves 48 in the suture fixation device 4. Alternately, the tine ends may be force-fit into grooves 48 in the suture fixation device so that engagement is maintained based on friction. Of course, it will be understood that the applier 42 may engage with the suture fixation device 4 in any other suitable way, such as a screw-in or snap configurations.

With the suture fixation device 4 in place relative to the second opening 54, the suture 3 may be tensioned so as to appropriately position the rotator cuff 2 relative to the humerus 1. At this point, the suture 3 may be fixed relative to the suture fixation device 4, such as by tying a knot with the suture ends. Thus, the suture fixation device 4 may provide not only a structure to support the suture knot, but also may spread the force of the suture 3 to portions of the relatively hard cortical bone surrounding or otherwise adjacent to the second opening 54. By having the suture fixation device 4 engage with this cortical bone, the suture fixation device 4 may provide a relatively stable and secure fixation point for the suture 3. The suture fixation device 4 may also incorporate a mechanism for knotless fixation of the suture, such as an interference pin, a locking passageway, a locking cap, etc.

Although in the illustrative embodiment described above both ends of the suture 3 are passed through the passageway 5 and secured at or near the second opening 54 of the passageway 5, the suture 3 may be secured in other ways, such as by passing one end of the suture 3 through the passageway 5 and passing another end of the suture 3 around the outside of the bone (e.g., over a portion of the greater tuberosity) where it is secured to the other suture end. In another embodiment, two passageways 5 may be formed through the bone and one end of the suture 3 may be passed through one passageway and the other end of the suture 3 may be passed through the other passageway. The suture ends may then be secured to each other at or near respective second openings of the passageways 5 on the lateral side of the humerus 1. In yet another embodiment, two or more first holes 51 may be formed so as to intersect with one or more second holes 52. Suture 3 may be passed through the two or more first holes 51 and be secured at the second opening 54 of the one or more second holes 52. Such an arrangement may allow for the use of a single second hole 52 and suture fixation device 4 to secure the rotator cuff at two or more points on the humeral head using two or more sutures that pass through different first holes 51. Other suture fixation techniques may be used as desired.

FIGS. 16A-B and 17A-B show illustrative embodiments of suture fixation devices 4 in accordance with the invention. In these embodiments, the suture fixation device 4 includes a restriction in a pathway through the suture fixation device 4 so that suture or other material passing through the suture fixation device is relatively freely moved in one direction through the pathway, but movement of the suture or other material in the other direction in the pathway is resisted. For example, movement of a suture though the suture fixation devices shown in FIGS. 16A and 17A in a direction to the left may be freely allowed, while movement of the suture toward the right may be resisted. This may aid in tensioning the suture 3 because the suture 3 may be pulled from the second hole 52 through the suture fixation device 4 until the rotator cuff or other tissue is appropriately positioned. Thereafter, tension on the suture may be temporarily released, e.g., in preparation for forming a knot, but movement of the suture back through the suture fixation device 4 may be resisted so that the rotator cuff or other tissue is maintained in place until the suture knot is tied or otherwise is secured.

Figure 16A:
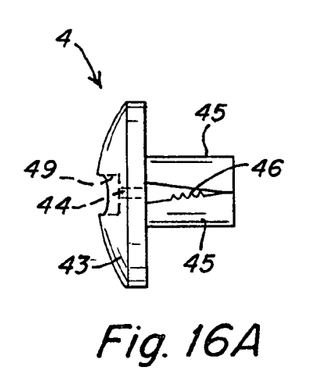
FIGS. 16A-B and 17A-B show side and rear views, respectively, of illustrative embodiments of suture fixation devices in accordance with the invention.
Figure 16B:
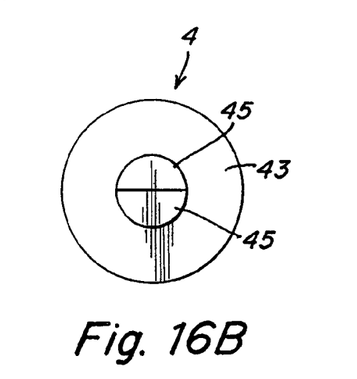

In the FIG. 16 embodiment, the suture fixation device includes an outer end having a flange portion 43 that is sized and arranged to contact the cortical bone adjacent the opening in the passageway at which the suture fixation device 4 is positioned, e.g., the second opening 54. One or more pathways 44 may be formed through the suture fixation device 4, such as by a hole or holes formed through the flange 43 (see also FIG. 15). Instead of having multiple holes, the pathway 44 may include a single slot arranged to receive one or more sutures. A recess 49 may be provided in the flange portion 43 to receive one or more knots, if formed with the suture(s) in the pathway 44. A pair of duck bill members 45 at an inner end of the suture fixation device 4 may extend rearwardly from the flange 43 and may be arranged as to be positionable in the second hole 54. The duck bill members 45 may be separated from each other by a groove that extends across the inner end of the suture fixation device 4 and be resiliently biased toward each other so as to resist the passage of suture or other material through the pathway 44. One or both of the duck bill structures 45 may include serrations 46 or other features that may aid in engaging a suture or other material. In the FIG. 16 embodiment, the groove separating the duck bill structures 45 extends to the flange portion 43 so that the structures 45 are pivotable at a point near the flange portion 43.

Figure 17A:
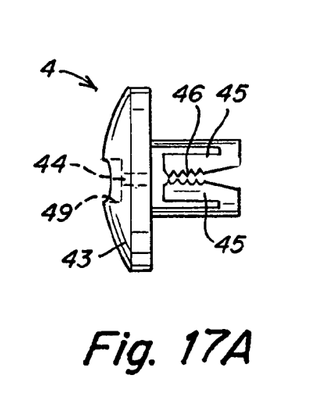
Figure 17B:
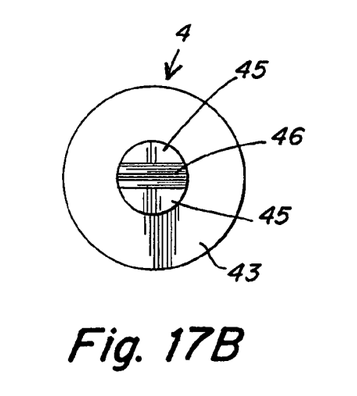

The FIG. 17 embodiment similarly includes a flange 43 and one or more pathways 44. Duck bill structures 45 are also provided. However, in this embodiment rather than being hinged at a point near respective connection points with the flange 43, the duck bill portions 45 are hinged at a point positioned away from the flange 43. Providing the effective hinge points for the duck bill structures 45 in this manner may provide improved engagement of the duck bill structures 45 with a suture or other material when the suture is urged to move from the outer end toward the inner end through the pathway 44. That is, if the suture is pulled to move toward the inner end, serrations 46 or other features will engage with the suture and increased force on the suture will cause an increased force urging the duck bill structures 45 to move toward each other and further squeeze the suture. The duck bill structures in the FIG. 16 and 17 embodiments or other suitable suture engagement arrangements (such as interference pins, locking caps, etc.) may provide a knotless fixation for the suture. Alternatively, the structures may resist movement of the suture so as to aid the surgeon's ability to maintain tension on the suture while forming a knot.

Although this embodiment depicts the flange of the device resting on the outer cortical surface of the bone, the device may be positioned in a hole which has a counterbore, or countersink, in order to prevent any interference between the flange and other bone or tissues that may come in contact with the site either at rest or during movement. Even in the case where the device is positioned in a counterbore or countersink feature, the device may contact cortical bone. Alternately, the device may only contact the outer, cortical surface of the bone, and not extend into a hole in the bone.

Of course, it should be understood that suture fixation devices may be provided in any suitable form. For example, the duck bill portions 45 extending from the flange 43 in the FIGS. 16 and 17 embodiments may be sized to closely fit into a mating hole formed in bone. This close fit may help in maintaining the suture fixation devices 4 in a desired position in the bone. Alternately, the duck bill structures 45 may be formed so as to be tapered on their outer surfaces. Thus, when the suture fixation device 4 is inserted into a hole in the bone, the tapered surfaces of the duck bill structures 45 may contact the sides of the hole and urge the duck bill structures to move toward each other as the suture fixation device 4 is pressed into the hole. In another embodiment, a portion of the suture fixation device 4 that is inserted into a hole may be threaded or otherwise be arranged so as to engage the hole and help prevent the suture fixation device from falling from the hole, e.g., before the suture is secured in place. There are many variations of the mechanism form to retain the suture with respect to the device. Some of these forms may require a knot for final fixation. Other capturing mechanisms may provide sufficient locking of the suture such that a knot is not required. Theses are typically known as "knotless" devices.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A surgical apparatus comprising:
   a guide apparatus constructed and arranged to be used in an arthroscopic procedure and to interact with a passageway through a bone formed by transverse, intersecting first and second holes, the first and second holes each being generally straight and leading into the bone from different positions, the guide apparatus including:
   first and second guide members each having distal and proximal ends, the first guide member having a first passage extending to the distal end of the first guide member, the second guide member having a second passage extending to the distal end of the second guide member, the distal ends of the first and second guide members being straight and the first and second passages being straight at the distal ends of the first and second guide members, the first guide member being constructed and arranged to be placed at a respective first arthroscopic passage and be selectively positioned at a site, the second guide member being constructed and arranged to be placed at a respective second arthroscopic passage that is different from the first arthroscopic passage and be selectively positioned at the site;
   a reference structure constructed and arranged to engage with the first and second guide members so that the first and second guide members are positioned in respective first and second positions relative to the reference structure with the first and second passages of the first and second guide members being transverse to each other; and
   a suture retriever movably arranged in the passage of the first or second guide member to extend from the distal end of the guide member, engage suture in the bone passageway, and retrieve the suture to the distal end of the guide member with the distal end of the guide member in the bone;
   wherein the distal end of the first guide member is arranged to be placed into the first hole so as to orient the first guide member, the reference structure and the second guide member relative to the bone for the second passage to guide a bone perforator in the formation of the second hole, wherein the second guide member is arranged to guide the bone perforator to form the second hole to be coaxial with the second passage, and wherein the passage of the first or second guide member is arranged to provide suture into the bone passageway for the suture retriever to extend from the distal end of the other guide member without suture being engaged with the suture retriever, engage the suture in the bone passageway and retrieve the suture to the distal end of the other guide member while the distal end of the other guide member is in the bone.

2. The apparatus of claim 1, wherein:
   the first and second guide members include first and second guide tubes, respectively, each of the first and second guide tube having a bore leading to the distal end that forms the first and second passage, respectively;
   and wherein the reference structure is constructed and arranged to engage with the first and second guide tubes so that when the first and second guide tubes are positioned in respective first and second positions relative to the reference structure, the distal ends of the first and second guide tubes are adjacent each other.

3. The apparatus of claim 2, wherein the distal ends of the first and second guide tubes include a threaded portion adapted to allow the first and second guide tubes to be screwed into the bone.

4. The apparatus of claim 2, wherein the reference structure includes first and second sleeves that respectively receive the first and second guide tubes, and the first and second guide tubes each include a stop that engages with the sleeves to position the distal ends of the first and second guide tubes adjacent each other.

5. The apparatus of claim 2, wherein the reference structure includes first and second sleeves that respectively receive the first and second guide tubes, and the first and second guide tubes each include at least one indicator mark to position the distal ends of the first and second guide tubes adjacent each other.

6. The apparatus of claim 2, wherein the first and second guide tubes each include a knob at a proximal end constructed and arranged to be handled by an operator to position the distal end into a corresponding hole.

7. The apparatus of claim 2, wherein the bore in the first and second guide tubes extends from the proximal end to the distal end.

8. The apparatus of claim 1, further comprising:
at least one bone perforator constructed and arranged to form a hole in bone while being guided in orientation by the guide apparatus.

9. The apparatus of claim 1, further comprising:
a suture fixation device constructed and arranged to be positioned relative to the passageway and aid in securing a suture at least partially positioned in the passageway.

10. The apparatus of claim 9, further comprising:
a suture fixation device applicator constructed and arranged to hold the suture fixation device and facilitate positioning of the suture fixation device at least partially in the passageway.

11. The apparatus of claim 9, further comprising:
a suture feed device constructed and arranged to facilitate positioning a suture through an opening in the suture fixation device.

12. The apparatus of claim 1, wherein the guide apparatus is constructed and arranged to be positioned relative to the first hole formed in the bone and define a location for the second hole in the bone.

13. The apparatus of claim 1, wherein the first arthroscopic passage is formed by a first arthroscopic cannula, and the second arthroscopic passage is formed by a second arthroscopic cannula.

14. The apparatus of claim 1, wherein the guide apparatus is arranged so that with the first and second guide members fixed relative to the first and second holes and at a known position relative to each other, a suture is positionable in the second passage of the second guide member and is retrievable via the first passage of the first guide member.

15. The apparatus of claim 1, wherein the first and second guide members and the reference structure are arranged so that with the first guide member positioned in a respective first arthroscopic cannula and in communication with the first hole, and the second guide member positioned in a respective second arthroscopic cannula different from the first arthroscopic cannula and in communication with the second hole, the reference structure is positioned outside of a body cavity.

* * * * *